United States Patent [19]

Gonzenbach et al.

[11] 4,406,828
[45] Sep. 27, 1983

[54] ODORANT AND/OR FLAVORANT SUBSTANCES

[75] Inventors: Hans U. Gonzenbach; Paul A. Ochsner, both of Gèneva, Switzerland

[73] Assignee: Givaudan Corporation, Clifton, N.J.

[21] Appl. No.: 175,789

[22] Filed: Aug. 6, 1980

[30] Foreign Application Priority Data

Aug. 10, 1979 [CH] Switzerland .................. 7355/79
Jun. 30, 1980 [CH] Switzerland .................. 5003/80

[51] Int. Cl.³ .............................................. C11B 9/00
[52] U.S. Cl. ................................... 252/522 R; 568/327
[58] Field of Search ..................... 568/327; 252/522 R

[56] References Cited

U.S. PATENT DOCUMENTS

| | | | |
|---|---|---|---|
| 2,857,433 | 10/1958 | Bruson et al. | 568/327 |
| 2,889,367 | 6/1959 | Beets et al. | 568/327 |
| 2,897,237 | 7/1959 | Carpenter et al. | 568/327 |
| 3,045,047 | 7/1962 | Davidson et al. | 568/327 |
| 3,078,319 | 2/1963 | Wood | 568/327 |
| 3,278,621 | 10/1966 | Stofberg et al. | 568/327 |
| 3,509,215 | 4/1970 | Wood et al. | 568/327 |
| 3,910,853 | 10/1975 | Kulka | 260/465 R X |
| 3,911,018 | 10/1975 | Hall et al. | 252/522 R |
| 3,978,126 | 8/1976 | Panneman | 260/340.5 R X |
| 4,013,682 | 3/1977 | Panneman | 260/340.5 R |
| 4,107,066 | 8/1978 | Schreiber et al. | 252/522 R |
| 4,162,256 | 7/1979 | Sprecker et al. | 568/327 |
| 4,162,266 | 7/1979 | Helminger et al. | 252/522 R |
| 4,260,511 | 4/1981 | Sprecker et al. | 252/522 R |
| 4,284,819 | 8/1981 | Sprecker et al. | 252/522 R |
| 4,302,363 | 11/1981 | Bruns et al. | 252/522 R |

FOREIGN PATENT DOCUMENTS 1811289 7/1969 Fed. Rep. of Germany .

OTHER PUBLICATIONS

Barclay et al., Can. J. Chem. 51, 1598, (1973).
Staab et al., Chem. Ber. 111, 2965–2981, (1978).
Chem. Abstracts 88: 22,458z, (1978).
Chem. Abstracts Reg. No. 62158-65-3.

Primary Examiner—Ethel G. Love
Attorney, Agent, or Firm—Robert F. Tavares

[57] ABSTRACT

This invention discloses novel odorant and/or flavoring compositions containing a substituted tetralin or indan of the general formula

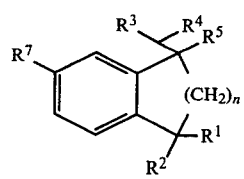

wherein R' represents —CN, —COCH$_2$R$^6$ or —COOCH$_2$R$^8$; R$^2$ through R$^8$ represent hydrogen or methyl and n represents 1 or 2.

The invention is also concerned with those novel tetralins and indans disclosed herein.

23 Claims, No Drawings

ODORANT AND/OR FLAVORANT SUBSTANCES

THE INVENTION

The present invention relates to novel odorant and-/or flavoring substances. More particularly, the invention is concerned with such compositions comprising a compound of the general formula

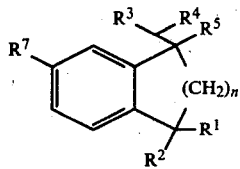

wherein the symbol $R^1$ represents —CN, —CO—CH$_2$—$R^6$ or —COO—CH$_2$—$R^8$, the symbols $R^2$ to $R^8$ represent hydrogen or methyl and the symbol n stands for 1 or 2.

In those cases wherein n=2, formula I represents the tetralin derivatives of formula Ia. In those cases wherein n=1 formula I represents the indan derivatives of formula Ib:

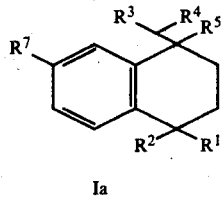 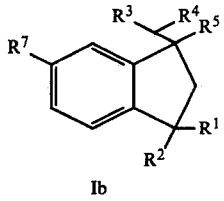

Ia  Ib wherein th symbols $R^1$ to $R^8$ have the significance given earlier.

The tetralin derivatives of formula Ia are all novel. With the exception of 1,1-dimethyl-3-cyano-indan, 1,1-dimethyl-3-acetyl-indan, 1,1,3-trimethyl-3-acetyl-indan and 1,1,3,6-tetramethyl-3-acetyl-indan, the indan derivatives of the formula Ib are also novel. The invention is also concerned with the novel tetralins and indans of formula I.

The compounds of formula I have particular organoleptic properties, on the basis of which they are excellently suited as odorant and/or flavouring substances. While the tetralins and indans of formula I all find utility as odorant and/or flavoring materials, the odorant and flavorant properties of the individual compounds show differences. In general, the tetralins of formula Ia are preferred.

The compounds of formula I demonstrate a number of general characteristics. On the basis of their natural olfactory notes and their tenacity (long lasting effect, especially with reference to freshness), the compounds of formula I are especially suitable for the modification of, for example, (α) known flowery compositions in which, for example, the citrus notes are to be emphasised (e.g. for cologne types and the like, extracts), (β) known fruity compositions, for example, of the raspberry type (extract types, compositions of feminine direction), (γ) known tobacco and wood compositions (extract types of masculine direction) and (δ) known compositions having green notes in which, in particular, desired rounding-off and harmonising effects are to be achieved.

Those compounds which are especially preferred are:

(a) 1,1-Dimethyl-4-propionyl-tetralin

This compound provides a very natural effect, extraordinarily long-lasting rose notes. The odour is a reminiscent of blonde tobacco, dried fruits, honey, damascone and 3-ethyl-1,1-dimethylcyclohex-3-ene-2-carboxylic acid (U.S. Pat. No. 4,113,663). In compositions these notes are hardly detectable. Instead, there are obtained surprising effects which, on the one hand, comprise a natural harmonic rounding-off and simultaneous accentuation of the citrus notes and, on the other hand, comprise a long-lasting harmony of the mixtures. This is true especially for the citrus notes. The compositions clearly remain fresher for a longer time than similar compositions without the compound.

(b) 1,1-Dimethyl-4-acetyl-tetralin

The odor of this compound is reminiscent of roses, tobacco, damascones, fruity, honey-like.

(c) 1,1,Dimethyl-indan-3-carboxylic acid methyl ester:

The odor of this compound is fruity, reminiscent of tobacco.

(d) 1,1-Dimethyl-4-cyano-tetralin

This compound has a pleasant fruity, tobacco-like odour, straw-like with a resemblance of patchouli and amber. Unexpected effects are found in compositions. 1,1-Dimethyl-4-cyano-tetralin confers volume to these and rounds them off in a harmonic manner. There is "produced" a naturalness which is extremely welcome in the case of purely synthetic compositions. At the same time the head notes are fixed, so that the compositions are balanced for a longer time.

(e) 1,1,7-Trimethyl-4-cyano-tetralin

The compound has properties similar to the preceding compound, but is more noble and with a slight musk character.

Other especially preferred compounds of formula I are:

(f) 1,1-Dimethyl-tetralin-4-carboxylic acid methyl ester, 1,1-dimethyl-tetralin-4-carboxylic acid ethyl ester and 1,1,4-trimethyl-tetralin-4-carboxylic acid methyl ester.

The compounds of formula I combine with numerous known natural or synthetic ingredients of odorant and-/or flavouring compositions, whereby the range of natural ingredients can embrace not only readily-volatile but also semi-volatile and difficultly-volatile substances, and the range of synthetic ingredients can embrace representatives from almost all classes of substances, as will be evident from the following compilation:

Natural products such as tree moss absolute, basil oil, bergamot oil, acetylated cedarwood oil (e.g. Vertofix, IFF or Cedartone, Givaudan), oak moss, galbanum oil, geranium oil, jasmine absolute and its substitute, lavender oil, lavandin oil, mastix absolute, neroli oil, patchouli oil, petitgrain oil Paraguay, sandalwood oil, vetiver oil, ylang-ylang oil, lemon oil, wormwood oil;

alcohols such as linalool, citronellol, geraniol, natural rhodinol, β-terpineol, phenylethyl alcohol, phenylpropyl alcohol, cinnamic alcohol, 3-methyl-5-(2',2',3',-trimethyl-cyclopent-3'-en-1'-yl)-pentan-2-ol (Sandalore ® Givaudan);

Aldehydes such as 3,5-dimethyl-cyclohex-3-ene-carboxaldehyde, decanal, methylnonylacetaldehyde, hydroxycitronellal, α-hexylcinnamaldehyde, cyclamen aldehyde, p-tert.butyl-α-methyl-dihydro-cinnamaldehyde (e.g. Lilial, ® Givaudan), citral;

ketones such as α-ionone, acetylcedrene, p-methylacetophenone, methyl ionone;

esters such as cedryl acetate, cis-3-hexenyl acetate, cis-3-hexenyl benzoate, ethyl acetoacetate, linalyl acetate, geranyl acetate, terpenyl acetate, phenylethyl acetate, styrallyl acetate, p-tert.butylcyclohexyl acetate, 4[4-methyl-3-pentenyl]-cyclohex-3-en-1-yl-carbinyl acetate (e.g. Myraldyl acetate, Givaudan), cinnamyl formate, benzyl acetate, benzyl salicylate, amyl salicylate, methyldihydrojasmonate, 3-ethyl-1,1-dimethyl-cyclohex-3-ene-2-carboxylic acid ethyl ester.

lactones such as γ-undecalactone, coumarin;

various additional components often used in perfumery such as musk compounds [musk ambrette, musk ketone, 12-oxa-hexadecanolide (e.g. Musk 174, Naarden), 1,1-dimethyl-4-acetyl-6-tert.butylindane, indole], p-menthane-8-thiol-3-one, eugenol, acetaldehyde-propylphenyl-ethyl acetal, methyl 1-methyl-cyclododecyl ether (e.g. Madrox, Givaudan).

The compounds of formula I can be used within wide limits which, for example, can extend from 0.1% in the case of detergents to 50% in the case of alcoholic solutions. It will be appreciated that these values are not limiting values, since the experienced perfumer can also achieve effects with still lower concentrations or can synthesise novel complexes with higher concentrations. The preferred concentrations vary between 0.5% and 25%. The compositions produced with compounds of formula I can be used for all kinds of perfumed articles (Eau do Cologne, eau de toilette, extracts, lotions, creams, shampoos, soaps, salves, powders, toothpastes, mouth washes, deodorants, detergents, tobacco etc).

The compounds of formula I can accordingly be used in the production of odorant compositions and, as will be evident from the foregoing compilation, using a wide range of known odorant substances. In the production of such compositions, the known odorant substances specified earlier can be used according to methods known to the perfumer such as, for example, according to W. A. Poucher, Perfumes, Cosmetics and Soaps 2, 7th Edition, Chapman and Hall, London, 1974.

As flavouring substances, the compounds of formula I can be used, for example, for the production, improvement, intensification, enhancement or modification of fruit or berry flavours, especially raspberry flavours, in foodstuffs (yoghurt, sweet goods etc), in luxury consumables (tea, tobacco etc) and drinks (lemonades etc).

The pronounced flavour qualities of the compounds of formula I enable them to be used as flavouring substances in low concentrations. A suitable range is, for example, 0.01 ppm–100 ppm, preferably 0.1 ppm–20 ppm, in the finished product (i.e. the flavoured foodstuff, luxury consumable or drink).

In the flavouring of, for example, tobacco the concentration can, however, also be higher and can have a wider range; for example, a range of 1 ppm–1000 ppm, preferably 50 ppm–500 ppm.

The compounds of formula I can be mixed with the ingredients of flavouring compositions or added to such flavourants in the customary manner. Among the flavourants contemplated in accordance with the invention there are to be understood flavouring compositions which can be diluted or dispersed in edible materials in a manner known per se. They contain, for example, about 0.1–10 wt.%, especially 0.5–3 wt.%. They can be converted according to methods known per se into the usual forms of use such as solutions, pastes or powders. The products can be spray-dried, vacuum-dried or lyophilised.

The known flavouring substances which are conveniently used in the production of such flavourants are either referred to in the foregoing compilation or can readily be concluded from the relevant literature (see, for example, J. Merory, Food Flavorings Composition, Manufacture and Use, Second Edition, The Avi Publishing Company, Inc., Westport, Conn. 1968, or G. Fenaroli, Fenaroli's Handbook of Flavor Ingredients, Second Edition, Volume 2, CRC Press Inc., Cleveland, Ohio, 1975)

For the production of such customary forms of use there can be used, for example, the following carrier materials, thickening agents, flavour-improvers, spices, auxiliary ingredients, etc:

Gum arabic, tragacanth, salts or brewers' yeast, alginates, carrageen or similar absorbents; indoles, maltol, dienals, spice oleoresins, smoke flavours; cloves, diacetyl, sodium citrate: monosodium glutamate, disodium inosine-5'-monophosphate (IMP), disodium guanosine-5-phosphate (GMP); or special flavouring substances, water, ethanol, propyleneglycol, glycerine.

The compounds of formula I can be prepared according to a number of novel routes as schematically represented in Formula Scheme I. Each route represents a novel sequence of steps which lead to the desired product of formula I. Each of the steps in the sequence, however, can be carried out using reactions and reaction conditions well known to those skilled in the art for performing such types of chemical transformations.

Each of these transformations are indicated on Formula Scheme I according to the following code.

| | |
|---|---|
| ⓐ | Alkenylations |
| ⓑ | Alkylations (Methylations) |
| ⓒ | Acylations |
| ⓓ | Cyclisations |
| ⓔ-ⓖ | Hydrolyses |
| ⓗ-ⓚ | Ketone synthesis |
| ⓛ | Manufacture of reactive acid derivatives |
| ⓜ-ⓞ | Manufacture of esters. |

Table I provides information concerning suitable methods and reagents as well as suitable and preferred reaction parameters for the individual process embodiments.

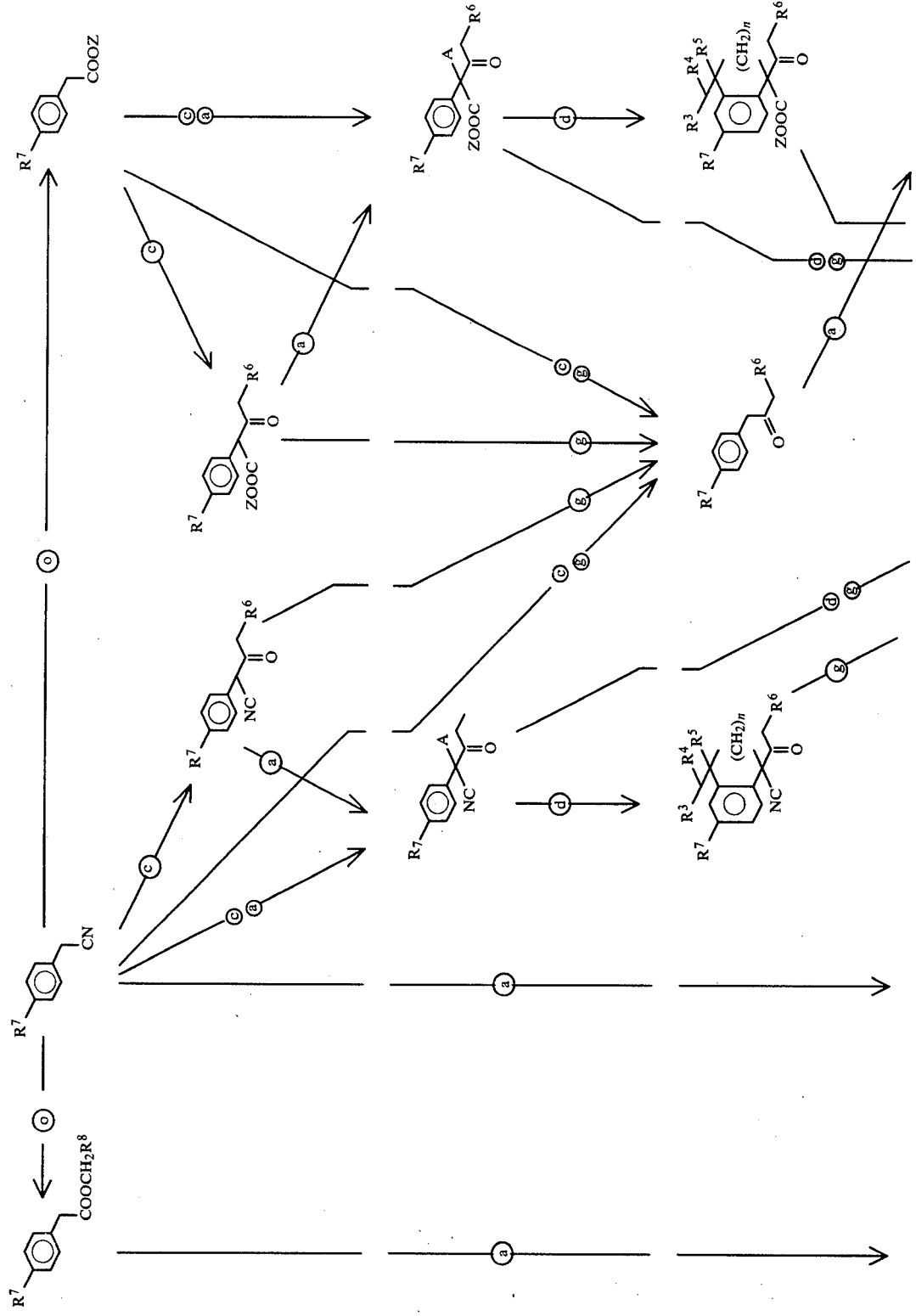

-continued
FORMULA SCHEME I
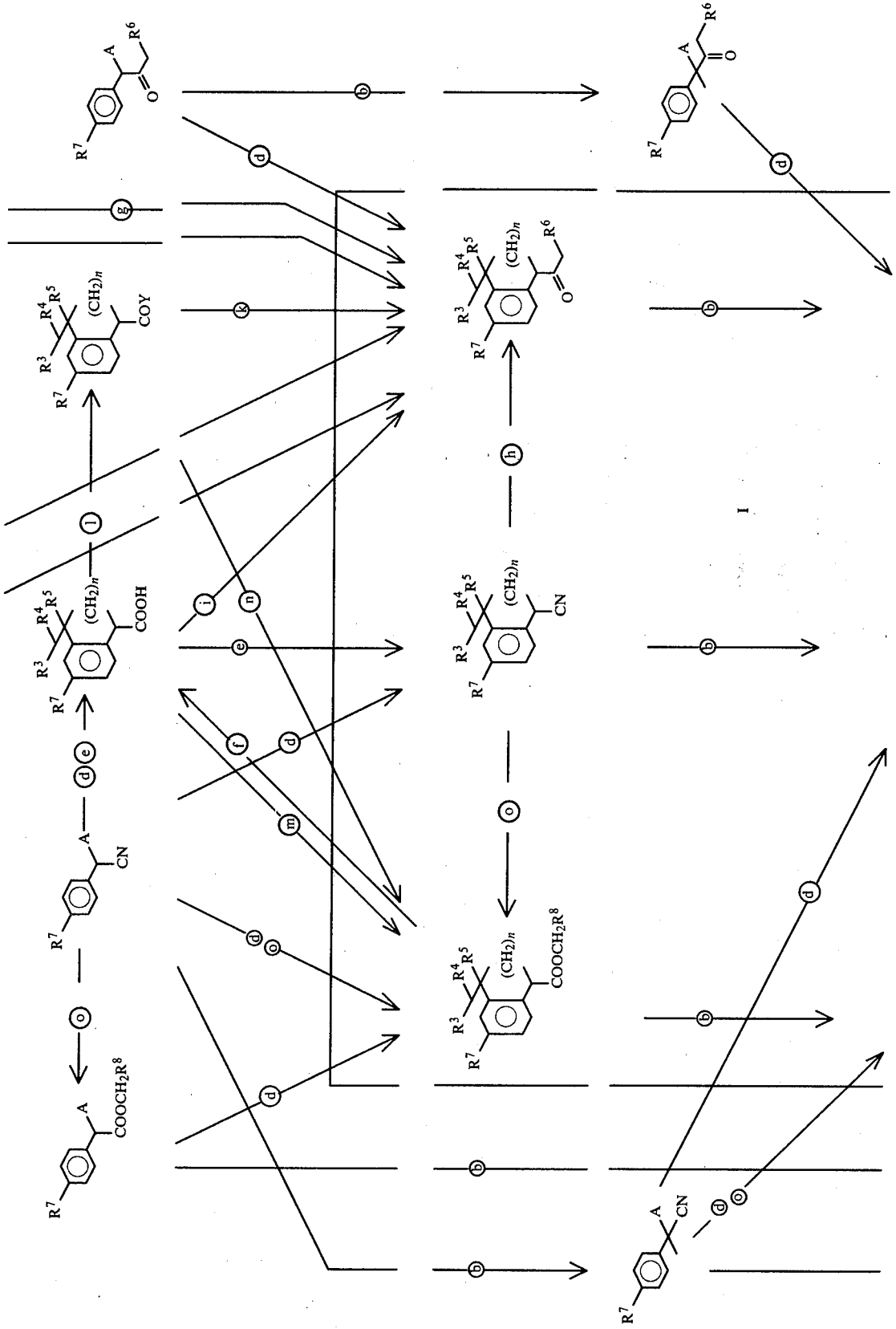

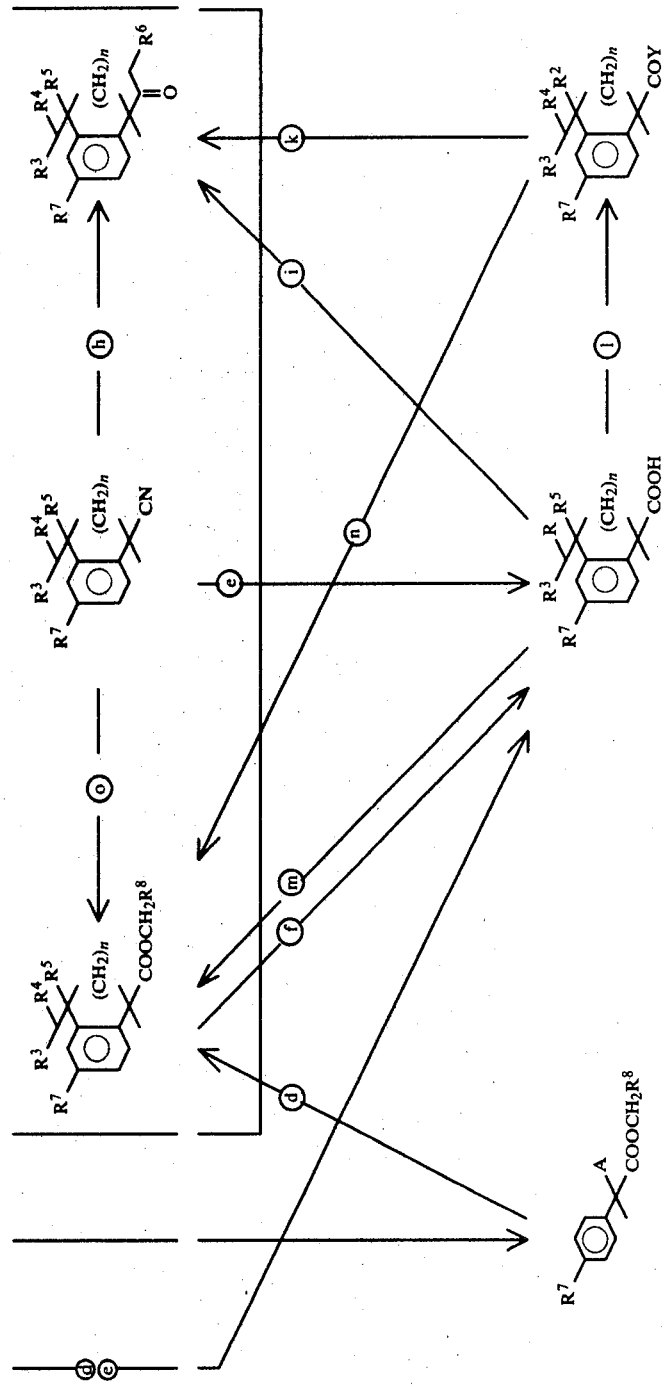

TABLE I

| | Reaction | Educt | Product | Reagent | Reaction conditions solv./cat./etc. | Remarks/Literature |
|---|---|---|---|---|---|---|
| (a) | Alkenylation | Ph–C(H)< | Ph–C(A)< | XA, XA' | (a) Under phase-transfer cond. (b) Classical e.g. +OH/+OK EtOH/EtONa Et₂O/NaH etc. | Jozef Dockx, Synthesis 1973, 441; ORGANIKUM, VEB, Deutscher Verlag der Wissenschaften, Berlin, 1967 |
| (b) | methylation | Ph–C(H)< | Ph–C(CH₃)< | XCH₃ | e.g. EtOH/EtONa Et₂O/NaH etc. | H. O. House, "Modern Synthetic Reactions" W. A. Benjamin, Inc., New York, Amsterdam 1965 |
| (c) | Acylation | Ph–C(NC)(ZOOC)H | Ph–C(NC)(ZOOC)–CH₂–C(O)–CH₂R⁶ | Y–COCH₂R⁶ (preferably ester) | | |
| (d) | Cyclisation | Ph–C(A)< | Ph–C<(CH₂)ₙ with R³,R⁴,R⁵ | PPA H₃PO₄ 85% | "mild" 50–100° C. | Cyclisation proceeds with retention of the nitrile function in contrast to E. GROCHOWSKI + T. BOLESLAWSKA Bull. Acad. Polon. Sci. Ser. Sci. Chim. 20, 297 (1972) |

Hydrolysis of

| | Reaction | Educt | Product | Reagent | Reaction conditions | Remarks/Literature |
|---|---|---|---|---|---|---|
| (e) | Nitrile | Ph–C(R²)(CN)< | Ph–C(R²)(COOH)< | Mineral acids (preferred), aqueous alkalis | e.g. H₂SO₄ 60% 100° C. | Under these conditions compounds of the type Ph–C(A)< simultaneously cyclise |
| (f) | Ester | Ph–C(R²)(COOZ)< | | Mineral acids, aqueous alkalis (preferred) | e.g. KOH / H₂O / EtOH | |

TABLE I-continued

| Reaction | Educt | Product | | Reagent | Reaction conditions solv./cat./etc. | Remarks/Literature |
|---|---|---|---|---|---|---|
| ⓖ keto-nitrile (keto-ester) followed by decarb-oxylation | 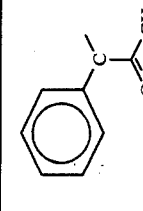 | 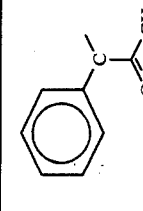 | sec. nitrile (ester) | mineral acids Carboxylic acids | e.g. H$_2$SO$_4$ 60% | Organic Synthesis, Coll. Vol. IV, 174 (1963) |
| | | | Tert. nitrile (ester) | strong acids | "vigorous" e.g. H$_2$SO$_4$ conc. or H$_3$PO$_4$ 100% HBr 48% glacial acetic acid 100°–150° C. | Steric hindrance in tert. nitriles (esters) require vigorous conditions, under which compounds of the type simultaneously cyclise 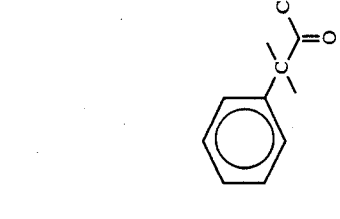 | ketone syntheses:

| Reaction | Educt | Product | Reagent | Reaction conditions | Remarks/Literature |
|---|---|---|---|---|---|
| ⓗ ex nitrile | 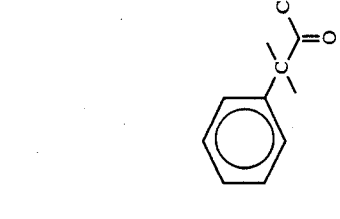 | 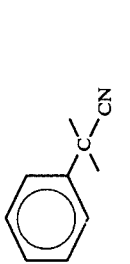 | MCH$_2$R$^6$ | CH$_3$MgX | Gen. F. Wingler, HOUBEN-WEYL 7/2a, 545 (1973) |
| ⓘ ex free acid | 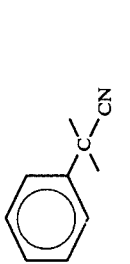 | | LiCH$_2$R$^6$ | esp. LiCH$_3$ | ibid. page 603 M. J. Jorgenson, Org. Reactions 18,1 |
| ⓚ ex reactive acid deriva-tive | 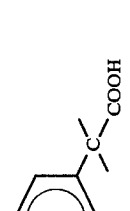 | | MCH$_2$R$^6$ | C$_2$H$_5$MgBr CuI as catalyst Y = Cl. | J. E. Dubois, M. Boussu, C. Lion THL 1971, 829. |
| ⓛ Manufacture of the react. acid derivatives | 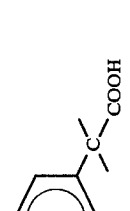 | 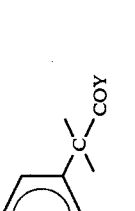 (Y = Cl preferred) | Gen. e.g. PCl$_3$ | 20–50° C. without solv. | ORGANIKUM/HOUBEN-WEYL ORGANIKUM/HOUBEN-WEYL |

TABLE I-continued

| Reaction | Educt | Product | Reagent | Reaction conditions solv./cat./etc. | Remarks/Literature |
|---|---|---|---|---|---|

Manufacture of the esters from (m) free acids

Ph–C(CH₃)₂–COOH  →Gen.→  Ph–C(CH₃)₂–COOCH₂R⁸   ORGANIKUM/HOUBEN-WEYL (n) react. acid derivatives Ph–C(CH₃)₂–COY  →Gen.→   ORGANIKUM/HOUBEN-WEYL (Y = Cl preferred)

TABLE I-continued

| Reaction | Educt | Product | Reagent | Reaction conditions solv./cat./etc. | Remarks/Literature |
|---|---|---|---|---|---|
| ⓒ Nitriles | 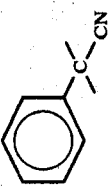 | 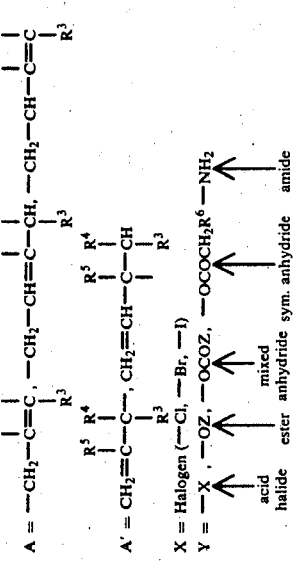 | ZOH/ $R^8CH_2OH$ mineral acid | EtOH/$H_2SO_4$ boiling point | Org. Synth. Coll. Vol. I, 270 (1958) |

Legends to Table I and Scheme I $A = -CH_2-C\equiv C-$, $-CH_2-CH=C-CH$, $-CH_2-CH-C\equiv C-$
  $\quad\quad\quad\quad R^3 \quad\quad\quad R^5\ R^4 \quad R^3 \quad\quad\quad R^5\ R^4 \quad\quad R^3$ $A' = CH_2=C-C-$, $CH_2=CH-C-CH-$
  $\quad\quad R^5\ R^4 \quad\quad\quad R^5\ R^4 \quad R^3$ X = Halogen (—Cl, —Br, —I)

Y = —X , —OZ, —OCOZ, —OCOCH$_2$R$^6$ —NH$_2$
  $\quad\quad\quad\quad\quad\quad$ ←————————————→ ←——→
  $\quad\quad$ acid $\quad\quad$ mixed
  $\quad\quad$ halide $\quad$ ester anhydride sym. anhydride $\quad$ amide Z = lower alkyl
PPA = polyphosphoric acid
M = organic bound metal, namely, for example, —Li, —MgX, —CdCH$_2$R$^6$, —Al(CH$_2$R$^6$)$_2$, —MnI, —ZnCH$_2^6$
ⓐ or ⓑ advantageously linked with ⓒ, addition of base being superfluous; the intermediately formed sodium (potassium, lithium etc) salt reacts with XA/XA'
ⓑ preferably linked with c
ⓐ + ⓒ preferably one step
ⓑ + ⓒ preferably one step ⋯⋯ signifies individual reagents or mixture of reagents.

{⋯⋯} signifies mixture of reagents.

The following Examples illustrate the present invention:

EXAMPLE 1

Preparation of the starting materials (A) 5-Methyl-2-phenyl-4-hexene nitrile 384 g (4.8 mol) of 50% sodium hydroxide and 12 g of hexadecyl-trimethylammonium bromide are placed in a 2-liter flask provided with a thermometer, stirrer and reflux condenser and there is added dropwise while stirring within 0.25 hour a mixture of 469 g of benzyl cyanide (4 mol) and 502 g (4.8 mol) of prenyl chloride[1]. During the addition the mixture warms and it is subsequently stirred for a further 3 hours at 60° C. After cooling, the mixture is poured on to 500 g of ice, extracted four times with ether and washed neutral with water. The phase separation can be facilitated by the addition of a small amount of alcohol. After drying over sodium sulphate, the ether is evaporated and the residue is fractionally distilled. There are obtained 444 g of 5-methyl-2-phenyl-4-hexene nitrile of boiling point 108°–109° C./3 mmHg; $n_D^{20}=1.5171$–72; yield 60%.

(1) Mixture of 1-chloro-3-methyl-2-butene and 3-chloro-3-methyl-1-butene.

(B) 4-Methyl-2-phenyl-4-pentene nitrile

If in the above process β-methallyl chloride is used in place of prenyl chloride, there is obtained 4-methyl-2-phenyl-4-pentene nitrile of boiling point 72° C./0.13 mmHg; $n_D^{20}=1.5203$.

(C) 5-Methyl-2-(p-tolyl)-4-hexene nitrile

From p-methyl-benzyl cyanide and prenyl chloride there is obtained in an analogous manner 5-methyl-2-(p-tolyl)-4-hexene nitrile of boiling point 89° C./0.03 mmHg; $n_D^{20}=1.5176$.

(D) Ethyl benzyl ketone

In a 2-liter flask provided with a thermometer, stirrer, dropping funnel and reflux condenser 600 ml of absolute alcohol are treated portionwise while stirring with 30 g of sodium metal and the mixture is held at reflux temperature until the metal has dissolved. Within 0.5 hour there is added dropwise to the boiling solution a mixture of 117.2 g of benzyl cyanide and 153.2 g of ethyl propionate and the mixture is heated for a further 3 hours. The alcohol is then distilled off and there are added 300 ml of toluene, followed by 250 ml of ice/water. The aqueous phase is separated, washed with 300 ml of toluene and then 540 g of 96% sulphuric acid are added. The mixture is held at reflux temperature until the evolution of carbon dioxide ceases, cooled, diluted with 250 ml of ice/water and extracted with two 300 ml portions of toluene. The toluene extracts are washed with water, with 10% sodium carbonate solution and again with water, dried over sodium sulphate and evaporated. Distillation gives 79 g of ethyl benzyl ketone of boiling point 69° C./3 mmHg; $n_D^{20}=1.5109$; yield 53%.

(E) 2-Methyl-5-phenyl-oct-2-en-6-one 192 g (2.4 mol) of 50% sodium hydroxide and 6 g of hexadecyl-trimethylammonium bromide are placed in a 2-liter flask provided with a thermometer, stirrer and reflux condenser and there is then added dropwise while stirring within 0.5 hour a mixture of 296 g (2 mol) of ethyl benzyl ketone and 251 g (2.4 mol) of prenyl chloride. The mixture is warmed to 60° C. and stirred for 3 hours. The mixture is left to cool and 500 ml of ice/water are added thereto. The mixture is extracted four times with ether and washed neutral with water. The phase separation can be facilitated by the addition of a small amount of alcohol. After drying over sodium sulphate, the ether is evaporated and a fractional distillation is then carried out. There are thus obtained 224 g of 2-methyl-5-phenyl-oct-2-en-6-one of boiling point 106° C./3 mmHg; $n_D^{20}=1.5092$–88; yield 75%.

(F) 2-Methyl-5-phenyl-hept-2-en-6-one

If in paragraph (E) ethyl benzyl ketone is replaced by methyl benzyl ketone, then there is obtained 2-methyl-5-phenyl-hept-2-en-6-one of boiling point 97° C./2 mmHg; $n_D^{20}=1.5135$.

(G) 2-Methyl-4-phenyl-hept-1-en-5-one

If ethyl benzyl ketone is reacted with β-methallyl chloride according to the foregoing details, then there is obtained 2-methyl-4-phenyl-hept-1-en-5-one of boiling point 93° C./3 mmHg; $n_D^{20}=1.5094$.

(H) 2-Methyl-4-phenyl-hex-1-en-5-one

Reaction of methyl benzyl ketone with β-methallyl chloride in accordance with the foregoing process yields 2-methyl-4-phenyl-hex-1-en-5-one of boiling point 85° C./3 mmHg; $n_D^{20}=1.5151$.

(J)(i) 5-Phenyl-oct-2-en-6-one

Ethyl benzyl ketone is reacted with crotyl chloride according to the foregoing details and there is obtained 5-phenyl-oct-2-en-6-one of boiling point 95° C./3 mmHg; $n_D^{20}=1.5102$.

(J)(ii) 5-Phenyl-hept-2-en-6-one

Methyl benzyl ketone is reacted with crotyl chloride or 3-chloro-1-butene in accordance with the foregoing details and there is obtained 5-phenyl-hept-2-en-6-one of boiling point 88° C./3 mmHg; $n_D^{20}=1.5190$. When 3-chloro-1-butene is used there is also obtained 3-methyl-5-phenyl-hex-1-en-5-one which is separated by distillation.

(K)(i) 5-Phenyl-oct-1-en-6-one

Ethyl benzyl ketone is reacted with 1-bromo-3-butene according to the foregoing details and there is obtained 5-phenyl-oct-1-en-6-one of boiling point 106° C./4 mmHg; $n_D^{20}=1.5088$.

(K)(ii) 2-Methyl-4-phenyl-but-1-en-4-oic acid methyl ester 24 g of sodium hydride in 400 ml of absolute tetrahydrofuran are place in a 1-liter flask provided with a thermometer, stirrer, reflux condenser and dropping funnel and heated at reflux temperature (70° C.). A mixture of 152 g of methyl phenylacetate and 91 g of β-methallyl chloride is then slowly added dropwise over a period of 1.5 hours. After completion of the addition, the mixture is heated for a further 2 hours and then left to cool. A small amount of methanol is added and then the mixture is then poured into 800 ml of water, extracted with ether, washed neutral, dried and evaporated. Distillation gives 101 g of 2-methyl-4-phenyl-but-1-en-4-oic acid methyl ester of boiling point 90° C./4 mmHg; $n_D^{20}=1.5078$; yield 50%. The distillation residue contains dibenzyl ketone.

(L) 4-Cyano-7-methyl-4-phenyl-oct-6-en-3-one 300 ml of dimethylformamide and 84 g of sodium alcoholate are introduced into a 1.5-liter flask provided with a thermometer, stirrer, dropping funnel and distillation head and there is added dropwise while stirring within 0.75 hours a mixture of 137 g of benzyl cyanide and 143 g of ethyl propionate. The solution warms to about 50° C. and a red colouration appears. The alcohol formed is distilled off under a slight vacuum and the solution is left to cool to room temperature, whereupon 146 g of prenyl chloride in 140 ml of dimethylformamide are added. The mixture is stirred at 60°–65° C. for 2.5 hours or until the solution has a neutral reaction. The solution is cooled, filtered, rinsed with hexane and evaporated. The residue is taken up in hexane, washed with water, dried over sodium sulphate, evaporated and distilled. There are obtained 150 g of 4-cyano-7-methyl-4-phenyl-6-en-3-one of boiling point 95° C./0.08 mmHg; $n_D^{20} = 1.5160$; yield 53%.

(M) 4-Methoxycarbonyl-7-methyl-4-phenyl-oct-6-en-3-one

In a manner analogous to that described in paragraph (L), by replacing benzyl cyanide with methyl phenylacetate there can be obtained 4-methoxycarbonyl-7-methyl-4-phenyl-oct-6-en-3-one of boiling point 108° C./0.08 mmHg; $n_D^{20} = 1.5202$.

(N) 1,1-Dimethyl-tetralin-4-carboxylic acid 1250 g of 60% sulphuric acid are placed in a 3-liter flask provided with a thermometer, stirrer and reflux condenser, heated to 60°–70° C. and 463 g of 5-methyl-2-phenyl-4-hexene nitrile are added dropwise thereto. After completion of the evolution of heat, the mixture is held at reflux temperature for 8 hours. After 15 hours, the mixture is extracted four times with ether. The organic phases are washed with water, dried over sodium sulphate and evaporated. There are obtained 501 g of crude product which are recrystallised from 625 ml of hexane. There are thus obtained 450 g of 1,1-dimethyl-tetralin-4-carboxylic acid of melting point 80°–81° C.; yield 88%.

(O) 1,1,7-Trimethyl-tetralin-4-carboxylic acid

Treatment of 5-methyl-2-(p-tolyl)-4-hexene nitrile according to N yields 1,1,7-trimethyl-tetralin-4-carboxylic acid of melting point 103° C.

(P) 1,1-Dimethyl-tetralin-4-carboxylic acid chloride 102 g of 1,1-dimethyl-tetralin-4-carboxylic acid are treated while stirring with 27.4 g of phosphorus trichloride and the mixture is stirred at 50° C. for 3 hours. This treatment is carried out while excluding moisture and conducting away the resulting hydrochloric acid gas. The upper phase is separated after 12 hours and distilled over a short Vigreux column. There are obtained 87 g of 1,1-dimethyl-tetralin-4-carboxylic acid chloride of boiling point 89° C./0.2 mmHg; $n_D^{20} = 1.5418$–20; yield 78%.

(Q) 1,1,7-Trimethyl-tetralin-4-carboxylic acid chloride

From 1,1,7-trimethyl-tetralin-4-carboxylic acid there is obtained in an analogous manner 1,1,7-trimethyl-tetralin-4-carboxylic acid chloride of boiling point 109° C./0.5 mmHg; $n_D^{20} = 1.5418$.

EXAMPLE 2

Compounds of formula I

(1)(i) 1,1-Dimethyl-4-cyano-tetralin 46.3 g of 85% phosphoric acid, 46.3 g of polyphosphoric acid, 250 ml of toluene and 92.6 g of 5-methyl-2-phenyl-4-hexene nitrile are mixed together and heated at 100° C. while stirring for 3 hours. The mixture is then poured on to ice. The mixture is now extracted with ether, washed with water, with 10% sodium carbonate solution and again with water until neutral, dried, evaporated and distilled in vacuo. There are obtained 85.3 g of 1,1-dimethyl-4-cyano-tetralin of boiling point 114° C./2 mm; $n_D^{20} = 1.5351$; yield 92%. Odour: pleasantly fruity, tobacco-like, after straw with a resemblance of patchouli and amber.

(1)(ii) 1,1,7-Trimethyl-4-cyano-tetralin

In an analogous manner, from 5-methyl-2-(p-tolyl)-4-hexene nitrile there is obtained 1,1,7-trimethyl-4-cyano-tetralin of boiling point 89° C./0.02 mmHg; $n_D^{20} = 1.5340$. Odour: similar to (3) but more like roses and tea.

(2)(i) 1,1-Dimethyl-3-cyano-indan

4-Methyl-2-phenyl-4-pentene nitrile yields, after an analogous treatment with polyphosphoric acid, 1,1-dimethyl-3-cyano-indan of boiling point 82° C./0.04 mmHg; $n_D^{20} = 1.5248$. Odour: earthy.

(2)(ii) 1,1-Dimethyl-indan-3-carboxylic acid methyl ester

2-Methyl-4-phenyl-but-1-en-4-oic acid methyl ester yields, after an analogous treatment with polyphosphoric acid, 1,1-dimethyl-indan-3-carboxylic acid methyl ester of boiling point 86° C./4 mmHg; $n_D^{20} = 1.5$. Odour: fruity, tobacco-like.

(2)(iii) 1,1-Dimethyl-tetralin-4-carboxylic acid ethyl ester 248 g of 1,1-dimethyl-tetralin-4-carboxylic acid in 1.740 liters of absolute alcohol are held at reflux temperature for 6 hours with 24.8 g of paratoluenesulphonic acid in a 3-liter flask provided with a thermometer, stirrer and reflux condenser. The excess alcohol is then distilled off under a slight vacuum and the residue is poured into ice/water. The mixture is extracted with ether, washed neutral, dried, filtered, evaporated and distilled, there being thus obtained 177 g of 1,1-dimethyl-tetralin-4-carboxylic acid ethyl ester of boiling point 74° C./0.03 mmHg; $n_D^{20} = 1.5153$; yield 63%. Odour: faint, jasmone-like.

(2)(iiii) 1,1-Dimethyl-tetralin-4-carboxylic acid methyl ester

By carrying out the foregoing esterification in methanol there is obtained 1,1-dimethyl-tetralin-4-carboxylic acid methyl ester of boiling point 77° C./0.01 mmHg; $n_D^{20} = 1.5250$. Odour: fruity.

(3) 1,1-Dimethyl-4-propionyl-tetralin 61.8 g of 1,1-dimethyl-4-cyano-tetralin in 100 ml of absolute ether are added dropwise while stirring to a Grignard solution prepared from 600 ml of ether, 34.7 g of magnesium shavings and 166 g of ethyl bromide. The mixture is held at reflux temperature for 6 hours, cooled and acidified with 10% hydrochloric acid. The aqueous phase is separated as rapidly as possible and held at reflux temperature for 1 hour. It is cooled, extracted with ether, washed neutral with water, dried over sodium sulphate and evaporated. Distillation in vacuo gives 39.4 g of 1,1-dimethyl-4-propionyl-tetralin of boiling point 75° C./0.05 mmHg; $n_D^{20} = 1.5263$; yield 55%. Odour: rose note, tobacco-like (light), dried fruits, berries, damascone, honey.

(4) 1,1-Dimethyl-4-propionyl-tetralin 36 g of 85% phosphoric acid, 36 g of polyphosphoric acid, 175 ml of toluene and 72 g of 2-methyl-5-phenyl-oct-2-en-6-one are heated together at 100° C. for 2 hours under a nitrogen atmosphere and while stirring. The mixture is left to cool, 250 ml of ice/water are added, the aqueous phase is separated and the organic phase is subjected to a steam distillation. The distillate is separated from the water and distilled in vacuo. There are obtained 50 g of 1,1-dimethyl-4-propionyl-tetralin of boiling point 75° C./0.05 mmHg; $n_D^{20} = 1.5263$; yield 70%. Odour: see (3).

(5) 1,1-Dimethyl-4-acetyl-tetralin

An analogous reaction to that described in paragraph 4 using 2-methyl-5-phenyl-hept-2-en-6-one yields 1,1-dimethyl-4-acetyl-tetralin of boiling point 69° C./0.07 mmHg; $n_D^{20} = 1.5333$. Odour: after roses, tobacco, damascone, fruity, honey-like.

(6)(i) 1-Methyl-4-propionyl-tetralin

5-Phenyl-oct-2-en-6-one or 5-phenyl-oct-1-en-6-one gives, in an analogous reaction, 1-methyl-4-propionyl-tetralin of boiling point 79° C./0.02 mmHg; $n_D^{20} = 1.5333$. Odour: fruity, somewhat minty.

(6)(ii) 1-Methyl-4-acetyl-tetralin

5-Phenyl-hept-2-en-6-one gives, in an analogous reaction, 1-methyl-4-acetyl-tetralin of boiling point 99° C./4 mmHg; $n_D^{20} = 1.5379$. Odour: methyl eugenol, straw.

(7) 1,1-Dimethyl-3-propionyl-indan

2-Methyl-4-phenyl-hept-1-en-5-one yields, under the specified conditions, 1,1-dimethyl-3-propionyl-indan of boiling point 64° C./0.03 mmHg; $n_D^{20} = 1.5199$. Odour: as (3), but somewhat weaker.

(8) 1,1-Dimethyl-3-acetyl-indan

2-Methyl-4-phenyl-hex-1-en-5-one yields, under analogous conditions, 1,1-dimethyl-3-acetyl-indan of boiling point 82° C./0.3 mmHg; $n_D^{20} = 1.5249$. Odour: as (3), but with an additional woody note.

(9) 1,1-Dimethyl-4-propionyl-tetralin

In a 3-liter flask provided with a thermometer and stirrer 200 g of phosphorus pentoxide are added while cooling to 500 g of 85% phosphoric acid and subsequently 150 g of 4-cyano-7-methyl-4-phenyl-oct-6-en-3-one are added at ca.50° C. The mixture is stirred at 105° C. until starting material is no longer present (gas chromatography/thin-layer). 1000 g of 48% hydrobromic acid and 500 g of glacial acetic acid are then added. After 12 hours, a further 200 g of 48% hydrobromic acid and 100 g of glacial acetic acid are added and the temperature is raised to 110° C. After a total reaction time of 30 hours, the mixture is cooled, ice is added and the mixture is extracted with ether, washed neutral with water, with 10% sodium hydroxide and again with water, dried over sodium sulphate and evaporated. Vacuum distillation gives 32 g of 1,1-dimethyl-4-propionyl-tetralin of boiling point 75° C./0.05 mmHg; $n_D^{20} = 1.5263$; yield 24%. Odour: see (3).

(10) 1,1-Dimethyl-4-propionyl-tetralin

The foregoing reaction can also be applied analogously to 4-methoxycarbonyl-7-methyl-4-phenyl-oct-6-en-3-one and then yields 1,1-dimethyl-4-propionyl-tetralin of boiling point 75° C./0.05 mmHg; $n_D^{20} = 1.5263$. Odour: see (3).

(11) 1,1-Dimethyl-4-acetyl-tetralin 16.8 g of 1,1-dimethyl-tetralin-4-carboxylic acid are treated dropwise in 200 ml of absolute ether under a nitrogen or argon atmosphere with 99.2 ml of a 2 molar solution of methyl lithium in ether (198.4 mmol). The mixture is stirred at room temperature for 1 hour and subsequently held at reflux temperature for a further 1 hour. The mixture is poured into saturated ammonium chloride solution, extracted with ether, washed neutral with water and dried over sodium sulphate. The ether is evaporated and the residue is fractionally distilled. There are obtained 8.4 g of 1,1-dimethyl-4-acetyl-tetralin of boiling point 69° C./0.07 mmHg; $n_D^{20} = 1.5333$; yield 50%. Odour: see (5).

(12) 1,1-Dimethyl-4-propionyl-tetralin 223 g (1 mol) of 1,1-dimethyl-tetralin-4-carboxylic acid chloride and 11 g of copper (I) iodide are placed in a 1-liter flask provided with a thermometer, stirrer, dropping funnel and reflux condenser and there is allowed to drop in from the dropping funnel at −10° C. to −5° C. a Grignard solution freshly prepared from 27 g (1.1 mol) of magnesium shavings and 122 (1.12 mol) of ethyl bromide in 500 ml of absolute ether. In so doing, the mixture must be diluted with a small amount of ether. The mixture is stirred for a further 5 hours while cooling and then the cooling source is removed. After the mixture has reached room temperature, it is poured into cold, saturated ammonium chloride solution, extracted with ether, washed neutral with water, dried over sodium sulphate and evaporated. Fractional distillation gives 138 g of 1,1-dimethyl-4-propionyl-tetralin of boiling point 75° C./0.05 mmHg; $n_D^{20} = 1.5263$; yield 64%. Ventilation can further improve the olfactory quality. Odour: see (3).

(13) 1,1-Dimethyl-4-acetyl-tetralin

If in the foregoing process the Grignard solution is prepared from methyl iodide, then there is obtained 1,1-dimethyl-4-acetyl-tetralin of boiling point 69° C./0.07 mmHg, $n_D^{20} = 1.5333$. Odour: see (5).

(14) 1,1,7-Trimethyl-4-propionyl-tetralin

By an analogous reaction using 1,1,7-trimethyl-tetralin-4-carboxylic acid chloride there is obtained 1,1,7-trimethyl-4-propionyl-tetralin of boiling point 90° C./0.08 mmHg; $n_D^{20} = 1.5270$. Odour: fruity, raspberries.

(15) 1,1,7-Trimethyl-4-acetyl-tetralin

By an analogous reaction using 1,1,7-trimethyl-tetralin-4-carboxylic acid chloride there is obtained 1,1,7-trimethyl-4-acetyl-tetralin of boiling point 73° C./0.02 mmHg; $n_D^{20} = 1.5309$. Odour: fruity, ionone-like.

(16) 1,1,4-Trimethyl-4-cyano-tetralin 81.5 g of 1,1-dimethyl-4-cyano-tetralin are added dropwise to 49 g of potassium tert.butylate in 400 ml of tert.butanol and the mixture is stirred at room temperature for 1 hour. At 5° C. there are then added dropwise 72 g of methyl iodide and the mixture is stirred for 15 hours without cooling. The bulk of the tert.butanol is distilled off, the residue is taken up in ether and washed neutral with water, dried over sodium sulphate and evaporated. The residue is distilled in vacuo and there are obtained 61 g of 1,1,4-trimethyl-4-cyano-tetralin of boiling point 85° C./0.25 mmHg; melting point 46° C.; yield 70%. Odour: resembling (3), but more intensive, woody.

(17) 1,1,4-Trimethyl-4-propionyl-tetralin 5.6 g of potassium tert.butylate are placed in 42.5 ml of tert.butanol and 10.8 g of 1,1-dimethyl-4-propionyl-tetralin are added dropwise thereto. The mixture is stirred for 1 hour, cooled to 5° C. and 8.5 g of methyl iodide are added. The mixture is stirred for a further 3 hours, a further 4.2 g of methyl iodide are added, the cooling source is removed and the mixture is stirred for a further 15 hours. The bulk of the tert.butanol is then removed by evaporation, the residue is taken up in ether, washed neutral with water, dried over sodium sulphate, evaporated and distilled. There are obtained 6 g of 1,1,4-trimethyl-4-propionyl-tetralin of boiling point 79° C./0.05 mmHg; $n_D^{20}=1.5249$; yield 52%. Odour: fruity, woody.

(18) (i) 1,1,4-Trimethyl-4-acetyl-tetralin

By analogous methylation of 1,1-dimethyl-4-acetyl-tetralin there is obtained 1,1,4-trimethyl-4-acetyl-tetralin of boiling point 112° C./4 mmHg: $n_D^{20}=1.5350$. Odour: woody, cedar-like, amber-like.

(18) (ii) 1,4-Dimethyl-4-propionyl-tetralin

By analogous methylation of 1-methyl-4-propionyl-tetralin there is obtained 1,4-dimethyl-4-propionyl-tetralin of boiling point 64° C./0.01 mmHg; $n_D^{20}=1.5303$. Odour: fruity, aromatic, green, woody, patchouli.

(18) (iii) 1,1,4,7-Tetramethyl-4-propionyl-tetralin

By analogous methylation of 1,1,7-trimethyl-4-propionyl-tetralin there is obtained 1,1,4,7-tetramethyl-4-propionyl-tetralin of boiling point 81° C./0.02 mmHg; $n_D^{20}=1.5260$. Odour: woody, roses, raspberries.

(19) 1,1,3-Trimethyl-3-propionyl-indan

By analogous methylation of 1,1-dimethyl-3-propionyl-indan there is obtained 1,1,3-trimethyl-3-propionyl-indan of boiling point 63° C./0.1 mmHg; $n_D^{20}=1.5150$. Odour: woody, ionone-like.

(20) 1,1,3-Trimethyl-3-acetyl-indan

By analogous methylation of 1,1-dimethyl-3-acetyl-indan there is obtained 1,1,3-trimethyl-3-acetyl-indan of boiling point 88° C./3 mmHg; $n_D^{20}=1.5158$. Odour: camphorous, patchouli.

(21) 1,1,4-Trimethyl-tetralin-4-carboxylic acid methyl ester 5.7 g of sodium hydride are placed in 80 ml of absolute tetrahydrofuran in a 500 ml flask provided with a thermometer, stirrer, reflux condenser and dropping funnel and 43.6 g of 1,1-dimethyl-tetralin-4-carboxylic acid methyl ester are added dropwise thereto. The mixture is then heated at reflux temperature for 1 hour. After cooling, 34 g of methyl iodide in 80 ml of absolute tetrahydrofuran are added dropwise and the mixture is held at reflux temperature for a further 1 hour. After cooling, a small amount of methanol is added, the mixture is poured into water and extracted with ether. The ether extracts are washed neutral, dried and evaporated. Distillation gives a quantitative yield of 1,1,4-trimethyl-tetralin-4-carboxylic acid methyl ester of boiling point 102° C./1.5 mmHg; $n_D^{20}=1.5219$. Odour: tobacco, similar to (3).

(22) 1,1,4-Trimethyl-tetralin-4-carboxylic acid ethyl ester

By analogous treatment of 1,1-dimethyl-tetralin-4-carboxylic acid ethyl ester there is obtained 1,1,4-trimethyl-indan-4-carboxylic acid ethyl ester of boiling point of 92° C./0.45 mmHg; $n_D^{20}=1.5119$. Odour: roses, faint.

EXAMPLE 3

In the following formulations U stands for 1,1-dimethyl-4-propionyl-tetralin and W stands for 1,1-dimethyl-indan-3-carboxylic acid methyl ester:

| 1. Woody base | |
|---|---|
| A: | Parts by weight |
| Basil oil | 30 |
| Methyl ionone | 50 |
| p-Tert.butylcyclohexyl acetate | 50 |
| Methyl dihydrojasmonate | 70 |
| Cedryl acetate crystalline | 100 |
| Sandalwood oil | 200 |
| Patchouli oil | 200 |
| Bergamotte oil | 200 |
| | 900 |

B: as above, but with the addition of 100 parts by weight of U.

C: as above, but with the addition of 100 parts by weight of W.

Olfactory evaluation

B is more pleasant and fresher than A, the bergamotte note stands out stronger.

After 24 or 48 hours, A is powdery on the smelling strips and is dominated by patchouli oil, whereas B has preserved its precious wood character and still smells cedar-like or sandalwood-like.

C is stronger and more woody than A and has a pleasant patchouli character. The tenacity is also substantially better in comparison to A.

| 2. Chypre base: | |
|---|---|
| A: | Parts by weight |
| Styrallyl acetate | 20 |
| Methylnonylacetaldehyde (10% in diethyl phthalate) | 20 |
| Vetiveryl acetate | 50 |
| Rhodinol | 50 |
| Patchouli oil | 50 |
| Tree moss absolute (50% in diethyl phthalate) | 50 |
| p-Tert.butyl-c-methylhydrocinamaldehyde | 100 |
| Hydroxycitronellal | 100 |
| Methyl ionone | 100 |
| Musk ambrette | 100 |

2. Chypre base:

| A: | Parts by weight |
|---|---|
| Coumarin | 100 |
| Bergamotte oil | 100 |
| | 840 |

B: as above, but with the addition of 160 parts by weight of U.

C: as above, but with the addition of 160 parts by weight of W.

Olfactory evaluation

A smells too strong after styrall acetate. In B on the other hand the bergamotte note is advantageously emphasised and the base is much fresher. After 24 or 48 hours, B is still substantially fresher than A; the jasmine-like, flowery or aldehydic note being fixed in B, whereas it disappears in A.

C has more volume than A. The combination of warm and animal-like notes comes into play pleasantly. The tenacity period is substantially better than in A.

3. Green base

| A: | Parts by weight |
|---|---|
| Citral | 10 |
| Wormwood oil | 10 |
| Mastix absolute | 20 |
| Basil oil | 80 |
| Methyl dihydrojasmonate | 100 |
| Alcohol (95°) | 130 |
| Linalyl acetate | 200 |
| α-Hexylcinnamaldehyde | 200 |
| Benzyl salicylate | 280 |
| | 950 |

B: as above, but with the addition of 50 parts by weight of U.

Olfactory evaluation

A is hard and unbalanced, whereas B is softer and more harmonic.

This difference appears much more clearly after 24 or 48 hours on the smelling strips. A is dominated by a wormwood note and the olfactory impression ends with a powdery note, while in B an impression of green freshness remains much longer.

4. Flowery base

| A: | Parts by weight |
|---|---|
| Laurin (hydroxycitronellal extra) | 760 |
| Linalool | 70 |
| n-Hexyl salicylate | 30 |
| Cyclamen aldehyde | 20 |
| Galbanum oil | 20 |
| | 900 |

B: as above, but with the addition of 100 parts by weight of U.

Olfactory evaluation

A is really one-sided. The cyclamen aldehyde and the galbanum stand out too strongly, this being especially observable in the case of the 24 or 48 hours value. B is embellished by a fuller flowery character and preserves this over a longer time.

5. Mens Cologne

| A: | Parts by weight |
|---|---|
| Bergamotte oil | 310 |
| Lemon oil | 120 |
| α-Hexylcinnamaldehyde | 100 |
| Methyl dihydrojasmonate | 60 |
| α-Ionone | 60 |
| Basil oil | 50 |
| Rhodinol (pure) | 40 |
| Eugenol | 40 |
| Neroli oil | 40 |
| Patchouli oil | 20 |
| Tree moss absolute (50% in propyleneglycol) | 20 |
| Vetivenyl acetate | 20 |
| Ylang-ylang oil | 20 |
| | 900 |

B: as above, but with the addition of 100 parts by weight of U.

C: as above, but with the addition of 100 parts by weight of W.

Olfactory evaluation

In contrast to A, B is much more pleasant and fresher, harmonic and modern. In the bottom B retains its fresh citrus/bergamotte note, while A is almost dull and woody.

C is richer and more rounded-off than A and preserves the harmony of wood and spice notes longer than A.

6. Classical Cologne

| A: | Parts by weight |
|---|---|
| Indole (10% in Carbitol) | 10 |
| Coumarin | 10 |
| Ylang-ylang oil | 20 |
| Neroli oil | 40 |
| Lavandin oil | 40 |
| Benzyl acetate | 40 |
| Eugenol (extra) | 40 |
| Citral | 60 |
| Methyl dihydrojasmonate | 100 |
| α-Hexylcinnamaldehyde | 100 |
| Lemon oil (Italian) | 100 |
| Bergamotte oil | 360 |
| | 920 |

B: as above, but with the addition of 80 parts by weight of U.

Olfactory evaluation

The novel tetralin underlines the citrus note and confers to the composition a hereby, lavender-like character. Accordingly, B is clearly preferred.

Thanks to a neroli note-fixing, which itself is still noticeable after 48 hours and is completely missing in A, B is still richer and sweeter than A after 24 hours. The olfactory complex in B is held together by the tetralin.

EXAMPLE 4

In the following formulation Examples V stands for 1,1-dimethyl-4-cyano-tetralin.

7. Rose base

| A: | Parts by weight |
|---|---|
| Phenylethanol | 200 |
| Citronellol (extra) | 150 |

7. Rose base

| A: | Parts by weight |
|---|---|
| Geraniol (pure) | 150 |
| Rhodinol (pure) | 80 |
| 8α,12-oxido-13,14,15 16-tetranorlabdane | 30 |
| Fixolide ® (6 acetyl-1,1,2,4,4,7-hexamethyl-1,2,3,4-tetrahydronaphthalene) | 100 |
| Lemarome N ® (mixture of ⅓ neral, ⅔ geranial) | 30 |
| Phenylacetic acid | 5 |
| Dipropyleneglycol | 155 |
| | 900 |

B: A with the addition of 100 parts by weight of V.

Olfactory evaluation

In comparison to A, B is clearly richer, has more volume, is less dry and therefore more honey-like. Although consisting only of synthetic odorant substances, B has a pronounced natural character and is reminiscent of tea roses.

8. Citrus base

| A: | Parts by weight |
|---|---|
| Linalyl acetate (synthetic) | 200 |
| Lemarome N ® | 150 |
| Laurin (hydroxycitronellal extra) | 100 |
| Linalool (synthetic) | 200 |
| $C_{11}$—aldehyde (10% in Carbitol) | 10 |
| Xylene musk | 20 |
| Fixolide ® | 50 |
| Dipropyleneglycol | 170 |
| | 900 |

B: A with the addition of 100 parts by weight of V.

Olfactory evaluation

The addition of V confers to the composition A a natural character, which in pure synthetic compositions is usually achievable only with difficulty. Moreover, B is richer and warmer and is harmonically completely rounded-off.

9. Citrus base

| A: | Parts by weight |
|---|---|
| Lylanyl acetate (synthetic) | 200 |
| Lemarome N ® | 150 |
| Laurin (hydroxycitronellal extra) | 100 |
| Linalool (synthetic) | 200 |
| $C_{11}$—aldehyde (10% in Carbitol) | 10 |
| Xylene musk | 20 |
| Fixolide ® | 50 |
| Dipropyleneglycol | 100 |
| Bergamotte oil | 70 |
| | 900 |

B: A with the a-dition of 100 parts by weight of V.

Olfactory evaluation

With respect to the natural character, A corresponds essentially to the composition 8B, because a natural note was produced by the bergamotte oil. Nevertheless, 9B is clearly preferred over 9A, since the head notes are fixed and B thus retains a natural harmony substantially longer.

10. Tuberose base

| A: | Parts by weight |
|---|---|
| α-Hexyl-cinnamaldehyde | 140 |
| Laurin (hydroxycitronellal extra) | 120 |
| Linalool (synthetic) | 100 |
| Terpineol | 100 |
| Prunolide (γ-nonalactone)(10% in dipropyleneglycol) | 20 |
| Peach pure (γ-undecalactone)(10% in dipropyleneglycol) | 20 |
| Balsam tolu | 140 |
| Jasmine absolute | 40 |
| Isoeugonel | 40 |
| Phenylacetaldehyde (10% in dipropyleneglycol) | 40 |
| Fixolide ® | 100 |
| Dipropyleneglycol | 40 |
| | 900 |

B: A with the addition of 100 parts by weight of V.

Olfactory evaluation

B is more fruity, more flowery and richer than A and, in contrast thereto, naturally rounded-off. After 6 hours, B has preserved its natural freshness, while A is only flat.

EXAMPLE 5

Fruity base in the direction of apricots

| A: | Parts by weight |
|---|---|
| α-Ionone | 160 |
| Dimethylbenzylcarbinyl butyrate | 100 |
| Ethylacetyl acetate (ethyl acetoacetate) | 60 |
| Galaxolide | 50 |
| Undecalactone | 30 |
| Palmarosa oil | 40 |
| Allyl ionone | 40 |
| Dirpopyleneglycol | 420 |
| | 900 |

B: as above, but with the addition of 100 parts by weight of W.

Olfactory evaluation

B is more natural and much more reminiscent of ripe apricots than A. B is more intensive.

EXAMPLE 6

Perfumery base in the direction of rose

| A: | Parts by weight |
|---|---|
| DGP (dipropyleneglycol) | 370 |
| Citronellol | 140 |
| Phenylethyl alcohol | 120 |
| Terpineol | 70 |
| Linalool | 60 |
| Dimethylbenzylcarbinyl acetate | 55 |
| Cinnamic alcohol substitute | 45 |
| Rosacetol (trichlorophenylmethylcarbinyl acetate) | 25 |
| Lilial ® Givaudan | 25 |
| α-amylcinnamaldehyde substitute | 10 |
| Phenylacetaldehyde dimethylacetal | 10 |
| Benzyl salicylate | 20 |
| | 950 |

B: as above, but with the addition of 50 parts by weight of W.

In spite of a slight loss of intensity, B is much more natural and finer and, in addition, possesses a welcome fruity note. B holds much longer and is accordingly clearly preferred by perfumers.

EXAMPLE 7

| Apricot flavour | | |
|---|---|---|
| | Parts by weight | |
| | A | B |
| Cinnamaldehyde | 0.5 | 0.5 |
| Terpenyl acetate | 1.25 | 1.25 |
| Methyl anthranilate | 1.25 | 1.25 |
| Linalyl acetate | 1.5 | 1.5 |
| Neroli oil bigarade | 2.5 | 2.5 |
| Geraniol | 5.0 | 5.0 |
| Amyl butyrate | 8.0 | 8.0 |
| Isoamyl acetate | 8.0 | 8.0 |
| Petitgrain oil (Paraguay) | 15.0 | 15.0 |
| Amyl valerate | 15.0 | 15.0 |
| Amyl formate | 20.0 | 20.0 |
| Ethyl oenanthate | 30.0 | 30.0 |
| α-Ionone | 30.0 | 10.0 |
| Vanillin | 80.0 | 80.0 |
| Benzaldehyde | 100.0 | 100.0 |
| Alcohol | 682.0 | 682.0 |
| U | | 20.0 |
| | 1000.0 | 1000.0 |

By the addition of the tetralin U to the composition A the fruity note is indeed weakened somewhat. However, there appears in addition (in B) a slightly woody note which together with the fruity note is strongly reminiscent of dried fruits (e.g. apricots). In the incorporation of B in tobacco the woody-fruity note can likewise be clearly established, the tobacco note being advantageously rounded-off.

Flavour B can be used as a so-called top flavour for the flavouring of tobacco (e.g. cigarettes), the guiding dosage being, for example, 80–120 kg, especially 100 g/kg, of tobacco.

EXAMPLE 8

| Raspberry flavour | |
|---|---|
| | Parts by weight |
| α-Irone | 1 |
| Cis-3-hexenyl acetate | 1 |
| Piperonyl acetate | 4 |
| Vanillin | 5 |
| Ethyl acetate | 5 |
| Ethylmaltol | 6 |
| Ethylacetoacetate | 15 |
| Raspberry ketone | 15 |
| Propyleneglycol | 945 |
| | 997 |
| U | 3 |
| | 1000 |

Dosage: for example 50 g to 100 liters of syrup.

By the addition of U to the foregoing composition the flavour thereof is significantly fuller and more rounded-off. In addition, the woody-fruity note which is typical of raspberry flavours in advantageously underlined.

Suitable dosages of U in the end product: 1–3 ppm, especially 1.5 ppm in household syrup; 2–4 ppm, especially 3 ppm in sweet goods.

I claim:

1. An odorant composition comprising an olfactorily effective amount of a compound of the general formula

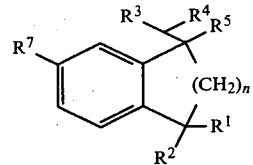

wherein:
$R^1$ represents —CO—CH$_2$R$^6$;
$R^2$ through $R^7$ represent hydrogen or methyl; and
n stands for 1 or 2,
and at least one other odorant compound.

2. A composition according to claim 1 comprising an olfactorily effective amount of a compound of the formula

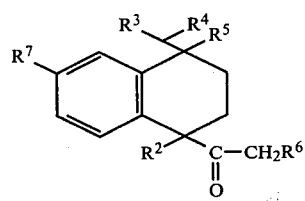

wherein $R^2$ through $R^7$ are as defined in claim 1.

3. A composition according to claim 1 comprising an olfactorily effective amount of a compound of the formula

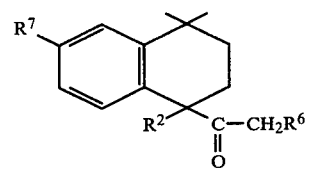

wherein $R^2$, $R^6$ and $R^7$ are as defined in claim 1.

4. A composition according to claim 3 comprising an effective amount of 1,1-dimethyl-4-acetyltetralin.

5. A composition according to claim 3 comprising an effective amount of 1,1-dimethyl-4-propionyltetralin.

6. A composition according to claim 3 comprising an effective amount of 1,1,7-trimethyl-4-propionyltetralin.

7. A composition according to claim 3 comprising an effective amount of 1,1,7-trimethyl-4-acetyltetralin.

8. A composition according to claim 1 comprising an olfactorily effective amount of a compound of the formula

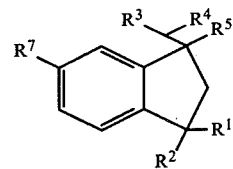

wherein $R^1$ through $R^7$ are as defined in claim 1.

9. A composition according to claim 1 comprising an olfactorily effective amount of a compound of the formula

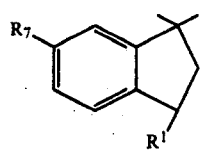

wherein $R^1$ and $R^7$ are as defined in claim 1.

10. A composition according to claim 9 comprising an effective amount of 1,1-dimethyl-3-propionyl-indan.

11. A composition according to claim 9 comprising an effective amount of 1,1-dimethyl-3-acetyl-indan.

12. A compound having the formula

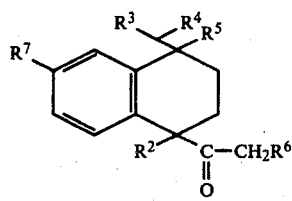

wherein $R^2$ through $R^7$ represent hydrogen or methyl.

13. A compound according to claim 12 having the formula

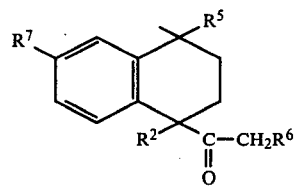

14. A compound according to claim 13 identified as 1,1-dimethyl-4-acetyltetralin.

15. A compound according to claim 13 identified as 1,1-dimethyl-4-propionyltetralin.

16. A compound according to claim 13 identified as 1,1,7-trimethyl-4-propionyltetralin.

17. A compound according to claim 13 identified as 1,1,7-trimethyl-4-acetyltetralin.

18. A compound according to claim 13 identified as 1-methyl-4-propionyltetralin.

19. A compound according to claim 13 identified as 1-methyl-4-acetyltetralin.

20. A compound according to claim 13 identified as 1,1,4-trimethyl-4-propionyltetralin.

21. A compound according to claim 13 identified as 1,1,4-trimethyl-4-acetyltetralin.

22. A compound according to claim 13 identified as 1,4-dimethyl-4-propionyltetralin.

23. A compound according to claim 13 identified as 1,1,4,7-tetramethyl-4-propionyltetralin.

* * * * *